US012788756B2

(12) United States Patent
Sekhavat et al.

(10) Patent No.: US 12,788,756 B2
(45) Date of Patent: Nov. 10, 2026

(54) FORMULATIONS FOR REDUCING HAIR LOSS AND/OR INCREASING HAIR REGROWTH

(71) Applicant: TRIPLE HAIR INC., Dieppe (CA)

(72) Inventors: Houfar Sekhavat, Dieppe (CA); Satish Asotra, Brampton (CA)

(73) Assignee: Triple Hair Inc., Dieppe (CA)

( * ) Notice: Subject to any disclaimer, the term of this patent is extended or adjusted under 35 U.S.C. 154(b) by 463 days.

(21) Appl. No.: 18/023,870

(22) PCT Filed: Aug. 27, 2021

(86) PCT No.: PCT/CA2021/051191
§ 371 (c)(1),
(2) Date: Feb. 28, 2023

(87) PCT Pub. No.: WO2022/040807
PCT Pub. Date: Mar. 3, 2022

(65) Prior Publication Data

US 2023/0310429 A1 Oct. 5, 2023

(30) Foreign Application Priority Data

Aug. 28, 2020 (CA) ................................ CA 3091554

(51) Int. Cl.

| | |
|---|---|
| ***A61K 31/506*** | (2006.01) |
| ***A61K 8/39*** | (2006.01) |
| ***A61K 8/49*** | (2006.01) |
| ***A61K 8/63*** | (2006.01) |
| ***A61K 9/00*** | (2006.01) |
| ***A61K 9/06*** | (2006.01) |
| ***A61K 9/12*** | (2006.01) |
| ***A61K 31/5575*** | (2006.01) |
| ***A61K 31/58*** | (2006.01) |
| ***A61K 47/10*** | (2017.01) |
| ***A61K 47/14*** | (2017.01) |
| ***A61Q 7/00*** | (2006.01) |

(52) U.S. Cl.
CPC .............. *A61K 31/506* (2013.01); *A61K 8/39* (2013.01); *A61K 8/4953* (2013.01); *A61K 8/63* (2013.01); *A61K 9/0014* (2013.01); *A61K 9/06* (2013.01); *A61K 9/122* (2013.01); *A61K 31/5575* (2013.01); *A61K 31/58* (2013.01); *A61K 47/10* (2013.01); *A61K 47/14* (2013.01); *A61Q 7/00* (2013.01)

(58) Field of Classification Search
CPC .......... A61Q 7/00; A61K 31/506; A61K 8/39; A61K 8/4953; A61K 8/63; A61K 9/0014; A61K 9/06; A61K 9/122; A61K 31/5575; A61K 31/58; A61K 47/10; A61K 47/14
See application file for complete search history.

(56) References Cited

U.S. PATENT DOCUMENTS

| | | | |
|---|---|---|---|
| 4,746,674 | A | 5/1988 | Pierpaoli et al. |
| 5,407,944 | A | 4/1995 | Goldman |
| 6,013,279 | A | 1/2000 | Klett-Loch |
| 6,030,948 | A | 2/2000 | Mann |
| 6,281,241 | B1 | 8/2001 | Elsner |
| 6,818,226 | B2 | 11/2004 | Reed et al. |
| 6,828,458 | B2 | 12/2004 | Sovak et al. |
| 7,704,533 | B2 | 4/2010 | Bruning et al. |
| 7,834,210 | B2 | 11/2010 | Gupta |
| 8,017,645 | B2 | 9/2011 | Schmid |
| 8,062,648 | B2 | 11/2011 | Schmid |
| 8,163,311 | B2 | 4/2012 | Bruning et al. |
| 8,470,833 | B2 | 6/2013 | Hu et al. |
| 8,481,015 | B2 | 7/2013 | Oblong et al. |
| 8,551,462 | B2 | 10/2013 | Goldstein et al. |
| 8,591,874 | B2 | 11/2013 | Oblong et al. |
| 8,758,733 | B2 | 6/2014 | Ahluwalia et al. |
| 8,802,117 | B2 | 8/2014 | Morganti |
| 8,871,773 | B2 | 10/2014 | Hu et al. |
| 8,877,762 | B2 | 11/2014 | Hu et al. |
| 12,053,541 | B2 | 8/2024 | Sekhavat |
| 2002/0012680 | A1 | 1/2002 | Patel et al. |
| CA 2309373 A1 | | 11/2000 | |
| CA 2309413 A1 | | 11/2000 | |
| CA 2392620 A1 | | 6/2001 | |
| CA 2206530 | | 10/2001 | |
| CA 2552607 A1 | | 7/2005 | |
| CA 2558150 A1 | | 9/2005 | |

(Continued)

FOREIGN PATENT DOCUMENTS

| | | | |
|---|---|---|---|
| CA | 2315395 | A1 | 7/1999 |
| CA | 2339231 | A1 | 2/2000 |

(Continued)

OTHER PUBLICATIONS

Gattefossé, "Topical Drug Deliver With Lipid Excipients," (2018). (Year: 2018).*

(Continued)

*Primary Examiner* — Jared Barsky
(74) *Attorney, Agent, or Firm* — Finnegan, Henderson, Farabow, Garrett & Dunner, LLP

(57) ABSTRACT

The invention relates to formulations comprising 2% to 10% minoxidil, 0.01% to 15% of a prostaglandin analogue, and, optionally 0.01% to 15% finasteride, and to formulations comprising 0.1 to 60% Dapsone and/or 0.1 to 20% Minocycline, tetracycline or doxycycline as an active ingredient. In one embodiment, the prostaglandin analogue is latanoprost. In a preferred embodiment, the composition comprises 5% minoxidil and 0.03% latanoprost. In another preferred embodiment, the composition further comprises 0.1% finasteride. The invention also relates to the use of the formulations to reduce hair loss and/or increase regrowth of hair in a human subject.

7 Claims, No Drawings

(56) References Cited

U.S. PATENT DOCUMENTS

| | | | | |
|---|---|---|---|---|
| 2003/0199590 | A1 | 10/2003 | Cagle et al. | |
| 2008/0206156 | A1 | 8/2008 | Cronk | |
| 2009/0098069 | A1 | 4/2009 | Vacca | |
| 2010/0048598 | A1 | 2/2010 | Kandavilli et al. | |
| 2011/0183016 | A1 | 7/2011 | Mailland et al. | |
| 2011/0195039 | A1 | 8/2011 | Isaacs | |
| 2012/0129789 | A1 | 5/2012 | Yoelin | |
| 2012/0277249 | A1 | 11/2012 | Andersson et al. | |
| 2012/0322776 | A1* | 12/2012 | Petersson | A61K 47/44 514/167 |
| 2012/0328549 | A1* | 12/2012 | Edelson | A61P 17/06 514/23 |
| 2013/0202683 | A1 | 8/2013 | McCook et al. | |
| 2015/0374603 | A1 | 12/2015 | Wu | |
| 2016/0213590 | A1* | 7/2016 | Sekhavat | A61K 8/361 |
| 2016/0346183 | A1 | 12/2016 | Sekhavat | |
| 2017/0100319 | A1 | 4/2017 | Sekhavat | |

FOREIGN PATENT DOCUMENTS

| | | | |
|---|---|---|---|
| CA | 2579784 | A1 | 3/2006 |
| CA | 2608031 | A1 | 11/2006 |
| CA | 2732582 | A1 | 2/2010 |
| CA | 2765284 | A1 | 12/2010 |
| CA | 2819859 | A1 | 6/2012 |
| JP | 2002537317 | A | 11/2002 |
| JP | 2008537960 | A | 10/2008 |
| JP | 2010504974 | A | 11/2010 |
| KR | 2001-0003063 | | 1/2001 |
| WO | 1995010284 | A1 | 4/1995 |
| WO | 2000048559 | A2 | 8/2000 |
| WO | WO00/050007 | A1 | 8/2000 |
| WO | WO2006/113505 | A2 | 10/2006 |
| WO | WO2008/042216 | A2 | 4/2008 |
| WO | 2011031990 | A1 | 3/2011 |
| WO | 2013078259 | A2 | 5/2013 |
| WO | 2013142295 | A1 | 9/2013 |
| WO | 2013181487 | A2 | 12/2013 |
| WO | WO 2015/176161 | | 11/2015 |

OTHER PUBLICATIONS

Keren et al., "The PDE4 inhibitor, apremilast, suppresses experimentally induced alopecia areata in human skin in vivo," J Dermatol Sci. Jan. 2015;77(1):74-6: PDE4 inhibitors can prevent hair loss. (Year: 2015).*

International Search Report and Written Opinion for International Patent Application PCT/CA2021/051191, dated Oct. 12, 2021 (9 pages).

Notice for Reasons of Rejection, Japanese Patent Application No. 2023-537443, Aug. 19, 2025, 6 pages.

International PCT Search Report dated Jul. 27, 2015 from PCT Application No. PCT/CA2015/000327, 4 pages.

Canadian Office Action dated Oct. 19, 2015 from Canadian Application No. 2903734, 3 pages.

Response to Canadian Office Action dated Oct. 22, 2015 from Canadian Application No. 2903734, 4 pages.

Canadian Notice of Allowance dated Nov. 30, 2015 from Canadian Application No. 2903734, 1 page.

Granted Claims from Canadian Patent No. 2903734, 4 pages.

International PCT IPRP dated Nov. 27, 2016 from PCT Application No. PCT/CA2015/000327, 5 pages.

European Search Report and Supplemental Search Report dated Oct. 18, 2016 in European Application No. 15795754, 10 pages.

Response to European Search Report dated May 16, 2017 in European Application No. 15795754, 9 pages.

Chinese Office Action dated Nov. 16, 2017 in Chinese Application No. 20158001707.7, 5 pages (with English translation, 6 pages).

Chinese Office Action dated Mar. 27, 2018 in Chinese Application No. 20158001707.7, 5 pages (with English translation, 6 pages).

Indian Office Action dated Jun. 15, 2018 in Indian Application No. 201627015405, 6 pages.

GlaxoSmithKline Publishes Japanese Dutasteride Hair Loss Study Results, GlaxoSmithKline (Sep. 14, 2014), http://www.hairlosscure2020.com/glaxosmithkline-publishes-japanese-dutasteride-hair-loss-study-results/.

Hamishehkar et al., Histological Assessment of Follicular Delivery of Flutamide by Solid Lipid Nanoparticles: Potential Tool for the Treatment of Androgenic Alopecia, Drug Dev. Ind. Pharm., 42(6):846-53 (Jun. 2016), 2 pages.

Japan Delays Dutasteride Drug for Male Pattern Hair Loss, Belgravia Centre, http://www.belgraviacentre.com (retrieved May 2016), 8 pages.

Levy et al., Female Pattern Alopecia: Current Perspectives, Int'l J. Women's Health, 5:541-556 (Aug. 2013), 19 pages.

Mcelwee et al., Promising Therapies for Treating and/or Preventing Androgenic Alopecia, Skin Therapy Letter, 17(6) (Jun. 2012), 8 pages.

Medical Wellness Center Website (Jun. 2013), http://www.medicalwellnesscenter.com, 10 pages, including Minoxidil Shampoo Webpage (Jun. 2013), http://xenicalwtloss.hypermart.net/MINOXIDILSHAMPOOHairLossPrescriptionINDEX, 1 page (total 11 pages).

Peytavi, A Randomized Double-Blind Placebo-Controlled Pilot Study to Assess the Efficacy of a 24-Week Topical Treatment by Latanoprost 0.1% on Hair Growth and Pigmentation in Healthy Volunteers with Androgenetic Alopecia, J. Am. Academy Derm., 66(5):794-800 (2012).

The End of Hair Loss and Balding by 2020, Brief Items of Interest (May 2016), http://www.hairlosscure2020.com/category/dutasteride/, 9 pages.

Uno et al., Effect of Latanoprost on Hair Growth in the Bald Scalp of the Stump-Tailed Macacque: A Pilot Study, Abstract, Acta Derm. Venereol., 82(1):7-12 (2002), 1 page.

* cited by examiner

FORMULATIONS FOR REDUCING HAIR LOSS AND/OR INCREASING HAIR REGROWTH

CROSS-REFERENCE TO RELATED APPLICATIONS

This application is a national stage application of International Application No. PCT/CA2021/051191, filed Aug. 27, 2021, and is based upon and claims the benefit of priority to Canadian Patent Application No. 3,091,554, filed Aug. 28, 2020, the entire contents of which are incorporated herein by reference.

FIELD OF INVENTION

The present invention relates to formulations for reducing hair loss and/or increasing hair regrowth. More specifically, the present invention relates to formulations for reducing hair loss and/or increasing hair regrowth comprising minoxidil, a prostaglandin analogue, and optionally finasteride. The formulations may also include a sulfone, such as Dapsone, which may also be used alone as an active ingredient for topical treatment of various alopecias. Formulations comprising minocycline, tetracycline or doxycycline as the active ingredient are also described.

BACKGROUND OF THE INVENTION

Hair loss, in one form or another, affects a vast majority of individuals at some point during their lifetime. Androgenetic alopecia (AGA) is hair loss (at scalp level) caused by the thinning of hair follicles. It is very common in men between the age of 19 and 70 years. Notably, more than 50% of Caucasian men in their fifties are affected by it. Women's hair loss mostly becomes an issue after menopause. Alopecia areata (AA) is believed to be an autoimmune disease that causes hair loss via inflammation. AA tends to affect individuals earlier than AGA, with children and teenagers being afflicted by either widespread scalp hair loss (AA totalis) or complete body hair loss (AA universalis) (Gilhar A et al., J Clin Invest 117(8); 2019-2027, 2007)

Individuals affected by AGA and AA show a diminution of their self-esteem that can effect negatively many facets of their lives.

There are several hair loss prevention products on the market. By way of example, minoxidil has been in use since the 1990s in topical form at 2% concentration (without prescription) and at 3% and 5% concentration (with prescription). While studies demonstrate the efficiency of 5% minoxidil over the 2% concentration, minoxidil is less than 40% effective in promoting regrowth of the hair. Minoxidil is considered the topical gold standard available for treatment of hair loss.

Another hair loss prevention product is finasteride. It is administered orally usually at a dosage of 1 mg/day. There are a number of side effects associated with the administration of finasteride including lowered libido, impotence, ejaculation disorders, allergic reactions, testicular pain, male infertility, male breast cancer and depression. At higher concentrations (5 mg), finasteride can cause benign prostate hyperplasia.

Latanoprost, a $PGF_{2\alpha}$ prostaglandin analog, is widely used in ophthalmology to treat open angle glaucoma and ocular hypertension. One of its side effects has been an augmentation of periocular hirsuteness, which includes a surge in the thickness, length and pigmentation of eyelashes which is to be distinguished from hair growth. Some of its other adverse effects are erythema, folliculitis, sensation of burning and erysipelas. A latanoprost ophthalmic solution has a concentration of 0.005%. It should be noted that scalp hair follicles and eyelash follicles are not identical and one cannot simply extrapolate from a drug effect on one type of hair to another.

SUMMARY OF INVENTION

According to an aspect of the present invention there is provided a formulation for reducing hair loss and/or growing hair comprising: about 2% to about 10% minoxidil; about 0.01% to about 5% finasteride; about 0.01% to about 1% of a prostaglandin analogue; and about 35% to about 45% Labrafil.

In one embodiment, there is provided a formulation in the form of a foam, the foam comprising: about 33.33% Labrafil M2130CS; about 8.33% Labrafil M1944CS; about 8.33% propylene glycol; about 5% Minoxidil; about 0.1% Finasteride USP; about 0.03% Latanoprost; about 5% Acrylic polymer; about 1.67% water; about 0.03% sodium hydroxide; about 0.33% Carbomer 934P; and about 38.18% absolute ethyl alcohol.

In another embodiment, there is provided a formulation in the form of a gel, the gel comprising: about 33.33% Labrafil M2130CS; about 8.33% Labrafil M1944CS; about 8.33% propylene glycol; about 5% Minoxidil; about 0.1% Finasteride USP; about 0.03% Latanoprost; about 0.016017% silicon dioxide; about 1.67% water; about 0.03% sodium hydroxide; about 0.33% Carbomer 934P; and about 42.83% absolute ethyl alcohol.

In another embodiment, there is provided a formulation in the form of an oil, the oil comprising: about 33.33% Labrafil M2130CS; about 8%8.33% Labrafil M1944CS; about 8.33% propylene glycol; about 5% Minoxidil; about 0.1% Finasteride USP; about 0.03% Latanoprost; about 0.17% Lavender or other fragrance; and about 44.71% Mineral oil, almond oil, avocado oil, argan oil, coconut oil, or combinations thereof.

In another embodiment, there is provided a formulation in the form of an emulsion, the emulsion comprising: about 33.33% Labrafil M2130CS; about 8.33% Labrafil M1944CS; about 8.33% Transcutol; about 8.33% propylene glycol; about 5% Minoxidil; about 0.1% Finasteride USP; about 0.03% Latanoprost; about 0.83% Triethanolamine acetate (TEA); about 1% Carbopol 940; and about 34.72% Water.

In another embodiment, there is provided a formulation in the form of a stick, the stick comprising: about 21.37% Hydrocarbon waxes, mineral waxes, hard waxes, microcrystalline waxes, or combinations thereof; about 6.67% Titanium Dioxide; about 33.33% Labrafil M2130CS; about 8.33% Labrafil M1944CS; about 8.33% propylene glycol; about 5% Minoxidil; about 0.1% Finasteride USP; about 0.03% Latanoprost; about 0.17% Lavender or other fragrance; and about 16.67% Mineral oil, almond oil, avocado oil, argan oil, coconut oil, or a combination thereof.

In a further embodiment, there is provided a formulation for reducing hair loss and/or growing hair comprising comprising: about 2% to about 10% minoxidil; about 0.01% to about 1% of a prostaglandin analogue; and about 35 to about 45% Labrafil.

In yet a further embodiment, there is provided a formulation in the form of a foam, the foam comprising: about 33.33% Labrafil M2130CS; about 8.33% Labrafil M1944CS; about 8.33% propylene glycol; about 5%

Minoxidil; about 0.03% Latanoprost; about 5% Acrylic polymer; about 1.67% water; about 0.03% sodium hydroxide; about 0.33% Carbomer 934P; and about 37.95% absolute ethyl alcohol.

In another embodiment, there is provided a formulation in the form of a gel, the gel comprising: about 33.33% Labrafil M2130CS; about 8.33% Labrafil M1944CS; about 8.33% propylene glycol; about 5% Minoxidil; about 0.03% Latanoprost; about 0.017% silicon dioxide; about 1.67% water; about 0.03% sodium hydroxide; about 0.33% Carbomer 934P; and about 42.93% absolute ethyl alcohol.

In another embodiment, there is provided a formulation in the form of an oil, the oil comprising: about 33.33% Labrafil M2130CS; about 8.33% Labrafil M1944CS; about 8.33% propylene glycol; about 5% Minoxidil; about 0.03% Latanoprost; about 0.17% Lavender or other fragrance; and about 44.81% Mineral oil, almond oil, avocado oil, argan oil, coconut oil, or combinations thereof.

In another embodiment, there is provided a formulation in the form of an emulsion, the emulsion comprising: about 33.33% Labrafil M2130CS; about 8.33% Labrafil M1944CS; about 8.33% Transcutol; about 8.33% propylene glycol; about 5% Minoxidil; about 0.03% Latanoprost; about 0.83% Triethanolamine acetate (TEA); about 1% Carbopol 940; and about 34.82% Water.

In another embodiment, there is provided a formulation in the form of a stick, the stick comprising: about 21.48% Hydrocarbon waxes, mineral waxes, hard waxes, microcrystalline waxes, or combinations thereof; about 6.67% Titanium Dioxide; about 33.33% Labrafil M2130CS; about 8.33% Labrafil M1944CS; about 8.33% propylene glycol; about 5% Minoxidil; about 0.03% Latanoprost; about 0.17% Lavender or other fragrance; and about 16.67% Mineral oil, almond oil, avocado oil, argan oil, coconut oil, or a combination thereof.

In a further embodiment, there is provided a formulation comprising: about 2% to about 6% Dapsone; about 5% to about 10% Transcutol; and about 35% to about 45% Labrafil.

In yet a further embodiment, there is provided a formulation in the form of an oil, the oil comprising: about 33.33% Labrafil M2130CS; about 8.33% Labrafil M1944CS; about 8.33% Propylene glycol; about 8.33% Transcutol; about 8.33% Absolute alcohol; about 3.33% Dapsone; about 0.17% Fragrance; and about 29.85% Mineral oil, almond oil, avocado oil, argan oil or coconut oil.

In yet a further embodiment, there is provided a formulation in the form of an oil, the oil comprising: about 33.33% Labrafil M2130CS; about 8.33% Labrafil M1944CS; about 8.33%

Propylene glycol; about 8.33% Transcutol; about 5% Dapsone; about 0.17% Fragrance; and about 36.51% Mineral oil, almond oil, avocado oil, argan oil or coconut oil.

In another embodiment, there is provided a formulation comprising: about 2% to about 4% Minocycline, tetracycline, or doxycycline; about 5% to about 10% Transcutol; about 35% to about 45% Labrafil; and a Cyclodextrin.

In yet a further embodiment, there is provided a formulation in the form of an oil, the oil comprising: about 33.33% Labrafil M2130CS; about 8.33% Labrafil M1944CS; about 8.33% Propylene glycol about 8.33% Transcutol; about 8.33% Absolute alcohol; about 3.33% Minocycline; about 0.17% Fragrance; and about 29.85% Mineral oil, almond oil, avocado oil, argan oil or coconut oil.

In another embodiment, there is provided a formulation comprising: about 2% to about 10% minoxidil; about 0.01% to about 5% finasteride; about 0.01% to about 1% of a prostaglandin analogue; about 0.1% to about 60% Dapsone, preferably about 2% to about 6% Dapsone; and about 0.1% to about 20% Minocycline, doxycycline or tetracycline, preferably about 2% to about 4% Minocycline, doxycycline or tetracycline.

According to another aspect of the present invention there is provided use of the formulations as described herein for reducing hair loss and/or increasing regrowth of hair in a human subject, as well as use of the formulations as described herein in the manufacture of a medicament for reducing hair loss and/or increasing regrowth of hair in a human subject.

DETAILED DESCRIPTION OF THE INVENTION

The invention relates to formulations comprising minoxidil, a prostaglandin analog, and optionally finasteride, which shows improved properties for the reduction of hair loss and for the increase of hair regrowth in human subjects, when compared to minoxidil, finesteride and latanoprost taken alone. Such compositions show superior improvements to those seen for each of the components of the compositions taken individually and the results obtained to date suggest that the improvements may be superior to those of the sum of the said components. The invention also relates to formulations comprising either Dapsone or minocycline as active ingredients.

In a preferred embodiment, the invention relates to formulations for topical or transdermal administration, in various forms.

Minoxidil or (6-(1-pipedidinyl)-2,4-pyrimidinediamine 3-oxide) has the following structural formula:

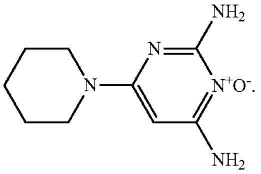

Minoxidil is a crystalline solid which has a solubility in mg/ml of 75 in propylene glycol, of 44 in methanol, of 29 in ethanol, of 6.7 in 2-propanol, of 6.5 in DMSO, of 2.2 in water, of 0.5 in chloroform, and of <0.5 in acetone. Minoxidil has a pKa of 4.61.

Finasteride or ((5α,17β)-N-(1,1-Dimethylethyl)-3-oxo-4-azaandrost-1-ene-17-carboxamide) has the following structural formula:

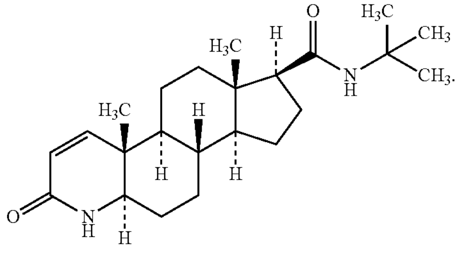

Finasteride is conventionally administered orally at a daily dose of 1 mg.

Finasteride is an anhydrous crystalline solid. Finasteride is freely soluble in chloroform, DMSO, ethanol, methanol, n-propanol; sparingly soluble in propylene glycol, polyethylene glycol 400; and very slightly soluble in 0.1N HCl and 0.1N NaOH. Finasteride is not soluble in water.

Finasteride is teratogenic and may result in birth defects. For at least this reason, it is often not recommended for use in premenopausal women, and it its use in women who are pregnant or planning to become pregnant is specifically advised against.

Latanoprost or ((5Z)-7-[(1R,2R,3R,5SO-3,5-Dihydroxy-2-[(3R)-3-hydroxy-5-phenylpentyl] cyclopentyl]-5-heptenoic acid 1-methylethyl ester) has the following structural formula:

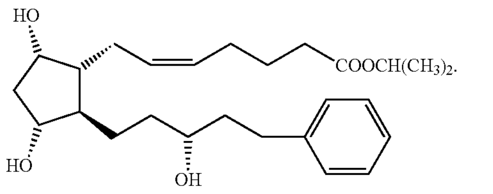

Latanoprost is an oil. Latanoprost is very soluble in acetonitrile; freely soluble in acetone, ethanol, ethyl acetate, isopropanol, methanol and octanol. It is practically insoluble in water.

Prostaglandins regulate a number of physiological functions. It has been found that most hair cell types are endowed with prostaglandin metabolism machinery and are thus able to produce $PGE_2$ and/or $PGF_{2\alpha}$. The epithelial part of the hair bulb is the main source of prostaglandin synthesis and interconversion. From Colombe et al. (*Prostaglandin Metabolism in Human Hair Follicle*, Exp Dermatol. 2007 Sep. 16(9): 762 to 769) and as minoxidil has also been found to enhance prostaglandin endoperoxide synthase-1 (PGHS-1) activity, this suggests that prostaglandins are involved in hair growth and differentiation control and that there is a link between prostaglandin synthesis and hair growth. Minoxidil has been demonstrated to be a potent activator of purified PGHS-1 by assaying oxygen consumption in prostaglandin $PGE_2$ production suggesting that the mechanism beyond the hair-growth stimulating effect of minoxidil is stimulation of $PGE_2$ synthesis (Michelet et al., *Activation of Cytoprotected Prostaglandin Synthase*-1 *by Minoxidil as a Possible Explanation for Its Hair Growth-Stimulating Effect*, J. Invest Dermatol 1997: 108: 205-209). This has been confirmed by the role of PGHS-2 in the control of hair cycle (Muller-Decker et al., *Expression of Cyclo-Oxygenase Isozymes During Morphogenesis and Cycling of Telage Hair Follicles in Mouse Skin*, J. Invest Dermatol 2003: 121: 661-668). It has been shown that the human hair follicle can sustain a complete $PGE_2$ and $PGF_{2\alpha}$ metabolism. Human hair follicles express (i) mPGES-1, mPGES-2 and cPGES which catalyse $PGE_2$ synthesis from $PGH_2$, (ii) AKR1C3/PGFS which converts $PGH_2$ into $PGF_{2\alpha}$ and (iii) CDR1 and AKR1C1 aldoketoreductase, which could control $PGE_2$/$PGF_{2\alpha}$ interconversion. As such, it has been shown that human hair follicles appear fully enzymatically equipped to self-process prostaglandin synthesis and metabolism, meaning $PGE_2$ and $PGF_{2\alpha}$ could be produced and inter-converted by hair follicles. While the composition tested comprised latanoprost, a $PGF_{2\alpha}$ prostaglandin analogue, it is surmised that other prostaglandin analogues can also be used given the role played by prostaglandin in hair growth and differentiation. By way of example, other suitable prostaglandin analogues include travoprost, bimatoprost, tafluprost and unoprostone.

In some formulations, a sulfone, such as Dapsone, can be used in conjunction with minoxidil and the prostaglandin analogues described above. This formulation can be particularly beneficial for the treatment of alopecia areata. In some embodiments, a steroid, such as Finasteride, can be added to the formulation to improve the functionality of the active ingredients. In yet a further embodiment, Dapsone may be used alone as a topical treatment for androgenic alopecia, female pattern alopecia, all forms of alopecia areata, including alopecia universalis, as well as frontal fibrosing alopecia and other inflammatory alopecias, in both children and adults.

In some formulations, minocycline serves as the active ingredient. Minocycline is a tetracycline antibiotic frequently used for the treatment of acne vulgaris. It may be applied topically or taken orally. In embodiments where minocycline is an active ingredient, the formulations may be used, for example, in treatment of androgenic alopecia, alopecia areata, various hair loss conditions in females including female pattern alopecia, and age-related hair loss.

The active ingredients can be delivered to the skin via the topical formulations described herein, or by using vehicles, such as nanoparticles and nanofibers (Goyal R et al., J Control Release 240:77-92, 2016) or cyclodextrin. When using nanoparticles for delivery, the active ingredient can be lodged inside and/or outside the nanoparticles. Cyclodextrins may be used as selective drug delivery systems, by enhancing solubility, stability and penetration of the active pharmaceutical ingredient (API) to the target area. Absorption of cyclodextrin is limited—it acts by delivering a payload, which is the API. Targeting groups/moieties may be chemically attached to the cyclodextrins, and the API is encapsulated and delivered to the target cells as led by the targeting group, with the API subsequently released at the place of desired action, acting selectively on the target cells.

Labrafil® (for example Labrafil® M21030CS or Labrafil® M1944CS) is a non-ionic water-dispersable surfactant that can be used as a co-eumlsifier in topical formulations to improve the stability of emulsions.

Propylene glycol, $C_3H_8O_2$, is a synthetic liquid substance that absorbs water and is miscible with a broad range of solvents. It may be used to absorb extra water and maintain moisture in medicines and cosmetics etc.

Carbomer 934P is a high molecular weight polymer compound used commonly in the cosmetic industry, more specifically an acrylic acid homopolymer crosslinked with allyl sucrose or allyl pentaerythritol designed for use in topical formulations of gels, emulsions and suspensions. Carbomers can absorb large amounts of water, increasing in volume up to 1,000 times to form gels and thick solutions that are stable and resistant to spoilage.

Carbopol® 940 is a water soluble polyvinyl carboxy polymer used as a viscosity enhancer, gelling agent, or suspension agent.

Transcutol® is a highly purified form of diethylene glycol monoethyl ether (DEGEE), a solubilizer associated with skin penetration enhancement in topical dosage forms.

Triethanolamine acetate (TEA) is an emulsion stabilizer and serves as a pH balancer in many different cosmetic products, such as cleansing creams, skin lotions, eye gels, moisturizers, shampoos, shaving foams, etc.

Absolute ethyl alcohol serves the function of a preservative.

fAcrylic polymers, such as Fixate™ G-100 (which is soluble in water and alcohol) may be included in the compositions of the present invention to increase the ease of brushing of the hair and for the adjustment of hair styling structure formation.

Waxes, such as hydrocarbon waxes, mineral waxes, hard waxes and/or micro-crystalline waxes may be included in the compositions of the present invention as hardening agents. Examples of hard waxes include but are not limited to: Mycra wax (melting point, "MP", of approximately 45°-55° C.), Beeswax (MP of approximately 61° C.-65° C.), Berry wax (MP of approximately 48° C.-54° C.) and Rice Bran wax (MP of approximately 79° C.-85° C.).

Further contemplated is the inclusion of the compositions of the present invention into a variety of types of formulations for topical use, including but not limited to: foams, gels, oils, emulsions and sticks.

Foams are known in the art to consist of a dispersion of particles in a continuous medium, and/or a colloidal system wherein the particles are gas bubbles and the medium is a liquid (i.e. a mass of small bubbles formed on or in liquid, typically by agitation or fermentation).

Gels are known in the art to be a sol in which the solid particles are meshed such that a rigid or semi-rigid mixture results. Cross-linking within the gel's polymer or colloidal network causes a gel to behave as a solid in its steady-state and makes it feel tacky. Most of the mass of a gel is liquid, such that gels are able to flow from the application of relatively low stress.

An oil is a nonpolar chemical substance that is a viscous liquid at ambient temperatures and is both hydrophobic and lipophilic.

An emulsion is a mixture of two immiscible liquids (i.e. two liquids that would not normally mix). An emulsion is a colloid where both phases are liquids, and contains tiny particles of one liquid suspended in another.

A stick as contemplated by the present invention is a solid substance that is suitable for topical application, having a wax base. A suitable stick will be solid (i.e. have a certain level of hardness, as would be understood by a person of skill in the art), yet also retain the properties of the wax component, so as to allow for easy application of the formulation to a subject, for example by rubbing onto the beard, mustache, eyebrows etc.

The formulations of the invention comprise 2% to 10% minoxidil, 0.01% to 15% of a prostaglandin analogue and, optionally, 0.01% to 15% finasteride, or the formulations comprise a sulfone such as Dapsone, or the antibiotic minocycline (or tetracycline or doxycycline) as the active ingredient. In an embodiment, the formulation comprises 2% to 5% minoxidil, 0.01% to 15% of a prostaglandin analogue and, optionally, 0.01% to 5% finasteride. In some embodiments, the formulation comprises minoxidil, a prostaglandin analogue, Dapsone, minocycline (or tetracycline or doxycycline) and optionally finasteride.

In a preferred embodiment, the formulation comprises 5% minoxidil and 0.03% of a prostaglandin analogue. In another preferred embodiment, the composition also comprises 0.1% finasteride. In yet another preferred embodiment, the prostaglandin analogue is latanoprost, travoprost, bimatoprost, tafluprost, unoprostone or a nitric oxide. In another preferred embodiment, the prostaglandin analogue is a composite drug such as latanoprosten (which is a composite of latanaprost and nitric oxide).

In another embodiment, the formulation comprises about 0.1% to about 60% Dapsone. In a preferred embodiment, the formulation comprises about 2% to about 6% Dapsone. In another preferred embodiment, the formulation comprises about 3.33% Dapsone. In yet another preferred embodiment, the formulation comprises about 5% Dapsone.

In another embodiment, the formulation comprises about 0.1% to about 20% minocycline, doxycycline or tetracycline and optionally a Cyclodextrin. In a preferred embodiment, the formulation comprises about 2% to about 4% minocycline. In yet another preferred embodiment, the formulation comprises about 3.33% minocycline.

In further embodiments, use of the formulations of the invention is contemplated for reducing hair loss and/or increasing regrowth of hair in human subjects, and/or for the manufacturing of a medicament for reducing hair loss and/or increasing regrowth of hair, such as hair found on scalps, beards or eyebrows, in human subjects. In another embodiment, some formulations of the present invention are contemplated for use in men and post-menopausal women. In another embodiment, some compositions of the invention are contemplated for use in pre-menopausal women.

Some non-limiting examples of preferred embodiments of these formulations of the present invention are shown in Tables 1 through 13, below.

TABLE 1

A Hair Foam for Men and Post-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Finasteride USP | Active ingredient | 0.06 g | 0.1 |
| Latanoprost (10,000 mcg/ml) | Active ingredient | 18 μl | 0.03 |
| Acrylic Polymer (Fixate ™ G-100—soluble in water & Alcohol) | Hair styling properties, flow, structure forming and ease of combing/brushing | 3 g | 5 |
| Aqua | Solvent for Carbomer | 1 mL | 1.67 |
| Sodium Hydroxide | Neutralization Agent | 0.02 mL | 0.03 |
| Carbomer 934P | Glidant | 0.2 g | 0.33 |
| Absolute ethyl alcohol | Solvent | QS to 60 ml | 38.18 |
| Total | | 60 mL | 100% |

TABLE 2

A Hair Foam for Pre-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Latanoprost (10,000 mcg/ml) | Active ingredient | 18 μl | 0.03 |

TABLE 2-continued

A Hair Foam for Pre-menopausal Women Comprising a Formulation of the Present Invention

| Component/Ingredient | Function | Quantity per unit (units in mL or as stated for each respective ingredient) | % |
|---|---|---|---|
| Acrylic Poymer (Fixate ™ G-100 - soluble in water & Alcohol) | Hair styling properties, flow, structure forming and ease of combing/brushing | 3 g | 5 |
| Aqua | Solvent for Carbomer | 1 mL | 1.67 |
| Sodium Hydroxide | Neutralization Agent | 0.02 mL | 0.03 |
| Carbomer 934P | Glidant | 0.2 g | 0.33 |
| Absolute ethyl alcohol | Solvent | QS to 60 ml | 37.95 |
| Total | | 60 mL | 100% |

The Hair Foam formulations of Tables 1 and 2 have an increased ease of application, an increased residence time, and increase the ease of combing/brushing of the hair. They also provide volume to the hair, increase hair shine and assist in the formation of the structure of a desired hair style.

TABLE 3

A Hair Gel for Men and Post-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Finasteride USP | Active ingredient | 0.06 g | 0.1 |
| Latanoprost (10,000 mcg/ml) | Active ingredient | 18 μl | 0.03 |
| Silicon Dioxide | Glidant | 0.01 | 0.017 |
| Aqua | Solvent for Carbomer | 1 mL | 1.67 |
| Sodium Hydroxide | Neutralization Agent | 0.02 mL | 0.03 |
| Carbomer 934P | Glidant | 0.2 g | 0.33 |
| Absolute ethyl alcohol | Solvent | QS to 60 ml | 42.83 |
| Total | | 60 mL | 100% |

TABLE 4

A Hair Gel for Pre-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Latanoprost (10,000 mcg/ml) | Active ingredient | 18 μl | 0.03 |
| Silicon Dioxide | Glidant | 0.01 | 0.017 |

TABLE 4-continued

A Hair Gel for Pre-menopausal Women Comprising a Formulation of the Present Invention

| Component/Ingredient | Function | Quantity per unit (units in mL or as stated for each respective ingredient) | % |
|---|---|---|---|
| Aqua | Solvent for Carbomer | 1 mL | 1.67 |
| Sodium Hydroxide | Neutralization Agent | 0.02 mL | 0.03 |
| Carbomer 934P | Glidant | 0.2 g | 0.33 |
| Absolute ethyl alcohol | Solvent | QS to 60 ml | 42.933 |
| Total | | 60 mL | 100% |

The Hair Gel formulations of Tables 3 and 4 have an increased ease of application and an increased residence time. They also provide volume to the hair and increase hair shine.

TABLE 5

A Hair Oil for Men and Post-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Finasteride USP | Active ingredient | 0.06 g | 0.1 |
| Latanoprost (10,000 mcg/ml) | Active ingredient | 18 μl | 0.03 |
| Lavender/other Fragrance | Fragrance | 0.1 | 0.17 |
| Mineral Oil/Almond Oil/ Avocado Oil/Argan Oil/ Coconut Oil | Solvent/Carrier | QS to 60 mL | 44.71f |
| Total | | 60 mL | 100% |

TABLE 6

A Hair Oil for Pre-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Latanoprost (10,000 mcg/ml) | Active ingredient | 18 μl | 0.03 |
| Lavender/other Fragrance | Fragrance | 0.1 | 0.17 |
| Mineral Oil/Almond Oil/ Avocado Oil/Argan Oil/ Coconut Oil | Solvent/Carrier | QS to 60 mL | 44.81 |
| Total | | 60 mL | 100% |

The Hair Oil formulations of Tables 5 and 6 have an increased ease of application and an increased residence time. They also provide volume to the hair, increase hair shine and assist in the formation of the structure of a desired hair style.

TABLE 7

A Hair Nano Emulsion for Men and Post-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Transcutol | Penetration enhancer, co-solvent | 5 | 8.33 |
| Propylene glycol | Solvent | 5 | 8.33 |
| Minoxidil | Active ingredient | 3 g | 5 |
| Finasteride USP | Active ingredient | 0.06 g | 0.1 |
| Latanoprost (10,000 mcg/ml) | Active ingredient | 18 μl | 0.03 |
| TEA | pH balancer and emulsion stabilizer | 0.5 | 0.83 |
| Carbopol ® 940 | Glidant/thickener | 0.6 | 1 |
| Water | Solvent/Carrier | QS to 60 mL | 34.72 |
| Total | | 60 mL | 100% |

TABLE 8

A Hair Nano Emulsion for Pre-menopausal Women Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Transcutol | Penetration enhancer, co-solvent | 5 | 8.33 |
| Propylene glycol | Solvent | 5 | 8.33 |
| Minoxidil | Active ingredient | 3 g | 5 |
| Latanoprost (10,000 mcg/ml) | Active ingredient | 18 μl | 0.03 |
| TEA | pH balancer and emulsion stabilizer | 0.5 | 0.83 |
| Carbopol ® 940 | Glidant/Thickener | 0.6 | 1 |
| Water | Solvent/Carrier | QS to 60 mL | 34.82 |
| Total | | 60 mL | 100% |

TABLE 9

A Hair Stick for Men and Post-menopausal Women Comprising a Formulation of the Present Invention

| Component/Ingredient | Function | Quantity per unit (units in mL or as stated for each respective ingredient) | % |
|---|---|---|---|
| Waxes (hydrocarbon waxes/mineral waxes/Hard waxes/ Micro-crystalline waxes) | Hardening agents | QS to 60 mL or grams. | 21.37 |
| Titanium Dioxide | Opacifying agent | 4 | 6.67 |
| Labrafil M2130CS | Co-solvent | 20 | 33.33 |
| Labrafil M1944CS | Co-solvent | 5 | 8.33 |

TABLE 9-continued

A Hair Stick for Men and Post-menopausal Women Comprising a Formulation of the Present Invention

| Component/Ingredient | Function | Quantity per unit (units in mL or as stated for each respective ingredient) | % |
|---|---|---|---|
| Propylene glycol | Solvent | 5 | 8.33 |
| Minoxidil | Active ingredient | 3 g | 5 |
| Finasteride USP | Active ingredient | 0.06 g | 0.1 |
| Latanoprost (10,000 mcg/ml) | Active ingredient | 18 μl | 0.03 |
| Lavender/other Fragrance | Fragrance | 0.1 | 0.17 |
| Mineral Oil/Almond Oil/ Avocado Oil/Argan Oil/ Coconut Oil | Solvent/Carrier | 10 | 16.67 |
| Total | | 60 mL or g | 100% |

TABLE 10

A Hair Stick for Pre-menopausal Women Comprising a Formulation of the Present Invention

| Component/Ingredient | Function | Quantity per unit (units in mL or as stated for each respective ingredient) | % |
|---|---|---|---|
| Waxes (hydrocarbon waxes/mineral waxes/Hard waxes/ Micro-crystalline waxes) | Hardening agents | QS to 60 mL or grams. | 21.48 |
| Titanium Dioxide | Opacifying agent | 4 | 6.67 |
| Labrafil M2130CS | Co-solvent | 20 | 33.33 |
| Labrafil M1944CS | Co-solvent | 5 | 8.33 |
| Propylene glycol | Solvent | 5 | 8.33 |
| Minoxidil | Active ingredient | 3 g | 5 |
| Latanoprost (10,000 mcg/ml) | Active ingredient | 18 μl | 0.03 |
| Lavender/other Fragrance | Fragrance | 0.1 | 0.16 |
| Mineral Oil/Almond Oil/ Avocado Oil/Argan Oil/ Coconut Oil | Solvent/Carrier | 10 | 16.67 |
| Total | | 60 mL or g | 100% |

The Hair Stick formulations of Tables 9 and 10 may be used at least on the beard and eyebrow area of a subject.

TABLE 11

A Hair Oil Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Transcutol | Penetration enhancer, co-solvent | 5 | 8.33 |
| Propylene glycol | Solvent | 5 | 8.33 |
| Absolute Alcohol | Solvent | 5 | 8.33 |
| Dapsone | Active ingredient | 2 g | 3.33 |

TABLE 11-continued

A Hair Oil Comprising a Formulation of the Present Invention

| Component/Ingredient | Function | Quantity per unit (units in mL or as stated for each respective ingredient) | % |
|---|---|---|---|
| Lavender/other Fragrance | Fragrance | 0.1 | 0.17 |
| Mineral Oil/Almond Oil/ Avocado Oil/Argan Oil/ Coconut Oil | Solvent/Carrier | QS to 60 mL | 29.85 |
| Total | | 60 mL | 100% |

TABLE 12

A Hair Oil Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Transcutol | Penetration enhancer, co-solvent | 5 | 8.33 |
| Propylene glycol | Solvent | 5 | 8.33 |
| Dapsone | Active ingredient | 3 g | 5 |
| Lavender/other Fragrance | Fragrance | 0.1 | 0.17 |
| Mineral Oil/Almond Oil/ Avocado Oil/Argan Oil/ Coconut Oil | Solvent/Carrier | QS to 60 mL | 36.51 |
| Total | | 60 mL | 100% |

TABLE 13

A Hair Oil Comprising a Formulation of the Present Invention

| Component/Ingredient | Function | Quantity per unit (units in mL or as stated for each respective ingredient) | % |
|---|---|---|---|
| Labrafil M2130CS | Co-solvent | 20 | 33.33 |
| Labrafil M1944CS | Co-solvent | 5 | 8.33 |
| Transcutol | Penetration enhancer, co-solvent | 5 | 8.33 |
| Propylene glycol | Solvent | 5 | 8.33 |
| Absolute Alcohol | Solvent | 5 | 8.33 |
| Minocycline | Active ingredient | 2 g | 3.33 |
| Lavender/other Fragrance | Fragrance | 0.1 | 0.17 |
| Mineral Oil/Almond Oil/ Avocado Oil/Argan Oil/ Coconut Oil | Solvent/Carrier | QS to 60 mL | 29.85 |
| Total | | 60 mL | 100% |

Various methods of preparation of the formulations of the present invention will be apparent to the skilled worker.

While the present invention has been described in connection with specific embodiments thereof and in a specific use, various modifications will occur to those skilled in the art. The scope of the claims should not be limited by the preferred embodiments or the examples but should be given the broadest interpretation consistent with the description as a whole.

What is claimed is:

1. A formulation for reducing hair loss and/or growing hair comprising:

a) about 2% to about 10% minoxidil;

b) about 0.01% to about 5% finasteride;

c) about 0.01% to about 1% of a prostaglandin analogue;

d) about 35% to about 45% of polyoxylglycerides, wherein the polyoxylglycerides comprise lauroyl polyoxylglycerides and oleoyl polyoxylglycerides in a 4:1 ratio;

e) diethylene glycol monoethyl ether; and f) propylene glycol.

2. The formulation according to claim 1, wherein the prostaglandin analogue is latanoprost, travoprost, bimatoprost, tafluprost, unoprostone, or a nitric oxide.

3. The formulation according to claim 1, wherein the lauroyl polyoxylglycerides are present in an amount of about 33% of the total volume of the formulation, and wherein the oleoyl polyoxylglycerides are present in an amount of about 8% of the total volume of the formulation.

4. The formulation according to claim 1, wherein the formulation is in the form of a foam, a gel, an oil, an emulsion, or a stick.

5. A method for reducing hair loss and/or increasing regrowth of hair in a human subject comprising administering to the human subject the formulation according to claim 1.

6. The method of claim 5, wherein the human subject suffers from at least one of androgenic alopecia, female pattern alopecia, alopecia areata, alopecia universalis, frontal fibrosing alopecia, or another inflammatory alopecia.

7. The formulation according to claim 2, wherein the prostaglandin analogue is latanoprost.

* * * * *